United States Patent [19]
Savithiry et al.

[11] Patent Number: 5,763,237
[45] Date of Patent: Jun. 9, 1998

[54] METHOD FOR PRODUCTION OF MONOTERPENE DERIVATIVES OF LIMONENE

[75] Inventors: Natarajan Savithiry, Okemos; Patrick J. Oriel, Midland, both of Mich.

[73] Assignee: Board of Trustees operating Michigan State University, East Lansing, Mich.

[21] Appl. No.: 857,873

[22] Filed: May 16, 1997

Related U.S. Application Data

[60] Provisional application No. 60/017,126, May 21, 1996.

[51] Int. Cl.$^6$ ............... C12P 7/26; C12P 7/24; C12P 7/02; C12N 1/20
[52] U.S. Cl. ............ 435/148; 435/136; 435/147; 435/155; 435/252.33; 435/252.5; 435/832
[58] Field of Search ............... 435/136, 147, 435/148, 155, 252.33, 252.5, 832

[56] References Cited

U.S. PATENT DOCUMENTS 5,487,988  1/1996  Chang et al.

OTHER PUBLICATIONS

Welsh, F. W., et al., Crit. Rev. Biotechnol. 9:105–169 (1989).
Krasnobajew, V., in Biotechnology, vol. 6a. Lieslich K. ed., Verlag Chemie, Weinheim Chapter 4, 105–107 (1984).
Chang, H. C., et al., J. Food Sci. 59:660–662 (1994).
Bauer, K., et al., Common Fragrance and Flavor Materials, VCH, Weinheim 46–53 (1990).
Chang, H.C. et al., J. Food Sci. 60:551–552 (1995).
Maniatis, T., et al., Molecular Cloning, Cold Spring Harbor Laboratory, New York 440,250, 251 (1982).
Nagasawa, T., et al., Appl. Environ. Microbiol. 54: 1766–1769 (1988).
Cadwallader, K.R., et al., in Food Science and Human Nutrition, Charalambous, G., ed., Elsevier, New York 57(1):241–244 & 248.

*Primary Examiner*—Herbert J. Lilling
*Attorney, Agent, or Firm*—Ian C. McLeod

[57] ABSTRACT

Enzymatic microbial degradation of limonene with simultaneous extraction of the degradation products with a non-water miscible organic solvent is described. Microbial degradation at elevated temperatures employing both an aqueous phase containing limonene and a neat limonene phase produced α-terpineol with additional production of carvone.

11 Claims, 3 Drawing Sheets

METHOD FOR PRODUCTION OF MONOTERPENE DERIVATIVES OF LIMONENE

This application claims the benefit of U.S. Provisional Application No. 60/017,126, filed May 21, 1996.

BACKGROUND OF THE INVENTION

(1) Summary of the Invention

The present invention relates to a novel method for producing monoterpene derivatives of limonene by extraction of an aqueous culture medium producing the derivatives with a relatively water immiscible organic solvent. Limonene is particularly preferred as the organic solvent. The extraction is performed simultaneously with the formation of the monoterpene derivatives in the culture medium so that the derivatives do not interfere with the culture. In particular, the present invention provides increased yields of the monoterpene derivatives at elevated temperatures.

(2) Description of Related Art

U.S. Pat. No. 5,487,988 to Chang and Oriel which describes metabolites of limonene. This patent does not solve the problem of low production of monoterpene derivatives from limonene in a culture medium.

Monoterpenes constitute a diverse group of C10-based plant secondary metabolites produced in part for defense against microbes and insects. Because of their unique organoleptic properties, certain monoterpenes utilized in fragrances and as food ingredients command some of the highest unit values among biotechnological products (Welsh, F. W., et al., Crit. Rev. Biotechnol. 9:105–169 (1989)). Microbial conversion of low value monoterpenes to higher value derivatives has been recognized for some time as an attractive opportunity, but has been thwarted by the lack of knowledge of microbial monoterpene pathways leading to a multiplicity of monoterpene metabolites (for review, see Krasnobajew, V., in Biotechnology, Vol. 6a. Lieslich, K. ed., Verlag Chemie, Weinheim (1984)). Because of its low cost and extensive availability as a waste citrus product (Bowen, E. R., Proc. Fla. State Hort. Soc. 88:305–308 (1975)), the monoterpene R-(+)-limonene has been selected as a target for directed microbial bioconversions. To help avoid problems arising from the microbial toxicity of this monoterpene, eubacterial thermophiles were targeted for investigation anticipating that their robust enzymes and growth ability in conditions favoring monoterpene volatilization might provide advantages in bioprocessing applications. In previous studies, a Bacillus stearothermophilus strain BR388 was isolated, which proved resistant to limonene toxicity, and which demonstrated production of perillyl alcohol and α-terpineol during growth on limonene (Chang, H. C., et al., J. Food Sci. 59:660–662 (1994)). The former compound has value as a flavorant (Krasnobajew, V., in Biotechnology, Vol. 6a. Lieslich, K. ed., Verlag Chemie, Weinheim (1984)), whereas the latter is extensively utilized in perfume manufacture (Bauer, K., et al., Common fragrance and flavor materials, VCH, Weinheim (1990)). In order to study and control the pathway metabolites, the entire pathway was cloned into *Escherichia coli* as a 9.6-kb plasmid insert, conferring to the new host growth on limonene as a sole carbon source and production of perillyl alcohol and α-terpineol (Chang, H. C., et al., J. Food Sci. 60:551,552 (1995)). It was proposed that limonene degradation in both the thermophile and recombinant proceeded by oxidation of the C-1 methyl to perillic acid with further breakdown utilizing the β fatty acid pathway, whereas α-terpineol was formed as a hydratase-catalyzed reversible side product (FIG. 1).

In particular, *Bacillus stearothermophilus* strain BR388 was isolated, proved resistant to limonene toxicity and demonstrated production of perillyl alcohol and α-terpineol during growth on limonene (Chang, H. C. and Oriel, P., J. Food Sci. 59:660–662 (1994)). The former compound has value as a flavorant (Krasnobajew, V., in Biotechnology, K. Lieslich. ed., Verlag Chemie, Weinheim V.6a (1984)), whereas the latter is extensively utilized in perfume manufacture (Bauer, K., et al., in: Common fragrance and flavor materials, VCH, Weinheim). The problem is the low amounts of conversion products from limonene.

SPECIFIC DESCRIPTION OF INVENTION

The present invention relates to an improvement in a method for microbial degradation of limonene in an aqueous culture medium to produce monoterpene derivatives which comprises: simultaneously with the degradation, extracting the monoterpene derivatives from the aqueous culture medium with a non-water miscible organic solvent for the monoterpene derivatives using a liquid-liquid contact for the extraction.

Preferably limonene is used as the solvent for the extraction. Other organic solvents for the products can be used for the extraction.

Figure 1:
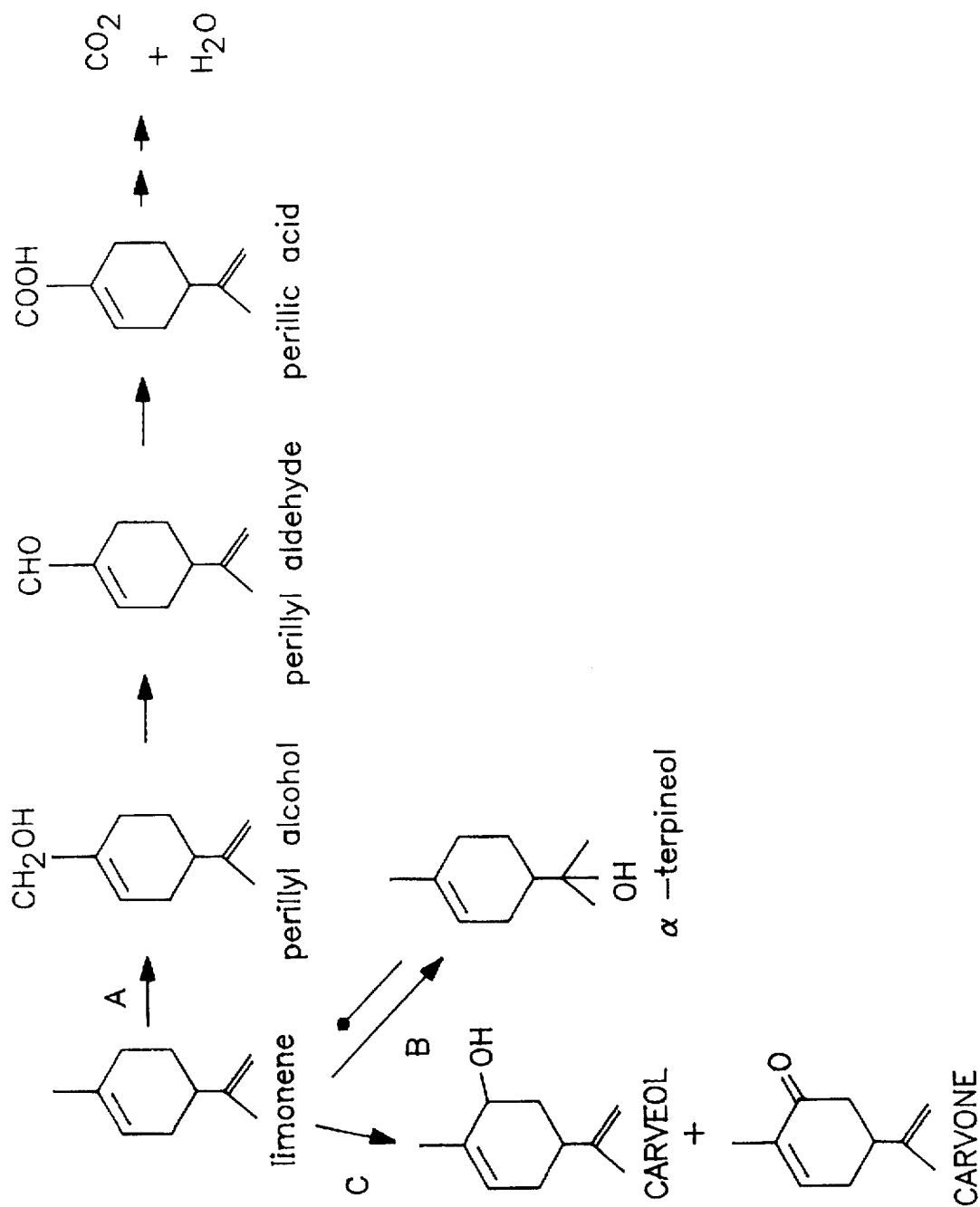
FIG. 1 is a diagram showing deduced is degradation pathways for *Bacillus stearothermophilus* BR 388 and *Escherichia coli* EC409A from limonene as the monoterpene. A denotes a deduced main pathway for limonene catabolism. B denotes limonene conversion to a dead end metabolite α-terpineol. C denotes conversion to carveol and carvone.
Figure 2:
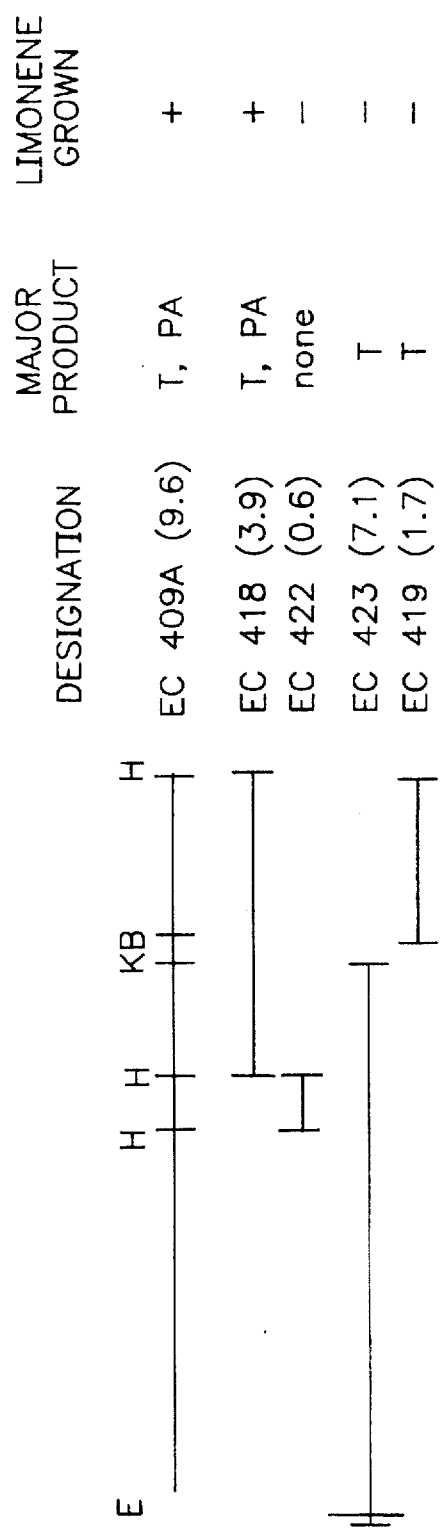
FIG. 2 is a partial restriction map of a 9.6 kb plasmid insert from *Bacillus stearothermophilus* in *Escherichia coli* EC409A. Abbreviations: E, EcoRI; B, BamHI; H, HindIII; K, KpnI. No cleavage sites were detected within the insert for restriction enzymes ClaI, PstI, SalI, and XbaI. Also shown are the vapor products, where T is terpineol and PA is perillyl alcohol.

In order to determine and control the pathway metabolites, the entire pathway of *Bacillus stearothermophilus* was cloned into *Escherichia coli* as a 9.6 kb plasmid insert, conferring to the new host the ability for growth on limonene as a sole carbon source and production of perillyl alcohol and α-terpineol (Chang, H. C. et al., J. Food Sci. 60:551–552 (1995)) and U.S. application Ser. No. 08/508, 818, filed Jul. 28, 1995. It appeared that limonene degradation in both the thermophile and recombinant proceeded by oxidation of the C-1 methyl to perillic acid with further breakdown utilizing the β fatty acid pathway, while α-terpineol was formed as a hydratase-catalyzed reversible side product (FIG. 2).

The preferred cultures used are those described in U.S. patent application Ser. No. 08/508,818, filed Jul. 28, 1995 by Oriel, Savithiry and Chang as inventors and owned by a common assignee, which is incorporated herein by reference. The *Bacillus stearothermophilus* (BR388) is deposited with the American Type Culture Collection, Rockville, Md. as ATCC 55596 as described in U.S. Pat. No. 5,487,988 to Oriel and Chang. The recombinant *Escherichia coli*

(EC409A) as ATCC 69817 is deposited under the Budapest Treaty with the American Type Culture Collection, Rockville, Md. as described in U.S. patent application Ser. No. 08/508,818. Other cultures are those of the prior art.

EXAMPLE 1

In particular whole cell bioconversion studies at elevated temperatures (40° to 60° C.) employing both an aqueous phase and neat limonene phase demonstrated significant production of α-terpineol with production of carvone in lesser amounts with certain cultures of *Bacillus stearothermophilus*.

EXAMPLE 2

Materials and Methods
Growth of Microorganisms

E. coli recombinants carrying B. stearothermophilus inserts were grown in M9 salts medium containing either yeast extract or the selected monoterpene. M9 minimal medium (Maniatis, T., et al., Molecular Cloning, Cold Spring arbor Laboratory, New York (1982)) contains per liter: $Na_2HPO_4$, 6 g; $KH_2PO_4$, 3 g; NaCl, 0.5 g; $NH_4Cl$, 1 g; pH 7.4. After autoclaving and cooling, 2 mL of 1M $MgSO_4$ and 0.1 mL of 1M $CaCl_2$ were added. Growth was carried out using 20 mL culture volumes in 40 mL serum bottles closed with Teflon-coated butyl stoppers and aluminum caps.

Limonene Hydratase Assay

Recombinant E. coli were grown in 50 mL LB medium containing 50 µg/mL ampicillin at 37° C. overnight. Cells were centrifuged and resuspended in 5 mL of 50 mM sodium phosphate buffer, pH 7.0, and disrupted by 30-s bursts of sonication with cooling on ice for 3–5 min. The crude enzyme extract resulting from centrifugation at 15,000 g for 30 min was assayed in a procedure adapted from Nagasawa et al. (Nagasawa, T., et al., Appl. Environ. Microbiol. 54:1766–1769 (1988)) using a 2 mL reaction mixture containing 1 mM 3-cyanopyridine in 50 mM phosphate buffer, pH 7.0. The reaction mixture was incubated at 55° C. for 20 minutes and stopped by addition of 0.2 mL 1M HCl. Nicotinamide product was determined using HPLC analysis (Waters HP1050 with 3.9 mm×15 cm NOVA C-218 column (Waters, Inc.). Peaks eluted using 60% acetonitrile in 5 mM sodium phosphate buffer, pH 7.7, were determined at 230 nm. Peaks were identified and quantified using known standards. One unit of activity is defined as the amount of enzyme that catalyzes formation of 1 µM/min nicotinamide under the specified conditions.

GC/MS Product Analysis

Aqueous culture supernatants were acidified to pH 2.0 with HCl extracted three times with ether, evaporated, and analyzed using GC/MS equipment (Hewlett Packard model 5890) and procedures described previously (Chang, H. C., et al., J. Food Sci. 59:660–662 (1994)). Samples of the limonene phase from bioreactor studies were injected directly.

Subcloning of E. coli EC409A Insert

The limonene pathway encoded in the 9.6 kb insert of EC409A was subcloned utilizing HindIII digestion, separation of the 8.2, 3.8 and 0.6 kb fragments by agarose gel electrophoresis, fragment recovery using electroelution, ligation into the HindIII site of pBluescript (SK+), and transformation into E. coli DH5α using standard procedures (Maniatis, T., et al., Molecular Cloning, Cold Spring Harbor Laboratory, New York (1982)). Similar procedures were employed to obtain subcloned fragments utilizing other restriction sites.

Two-Phase Bioreactor Studies

To examine formation of α-terpineol in the whole-cell two phase bioreactor shown schematically in FIG. 3 described hereinafter, 5 mL of neat limonene and 50 mL of EC423 cell suspensions ($10^9$ cells/mL) in M9 salts were shaken in a gyratory water bath at 250 rpm in 125 mL screw cap bottles at varied temperatures. Samples of aqueous and limonene phases were taken for GC/MS analysis after various periods of incubation of the cell suspension.

Results
Subcloning of the Limonene Hydratase Gene

Both α-terpineol and perillyl derivatives were metabolic products formed during growth of the recombinant E. coli EC409A on limonene which suggested that both limonene hydratase and methyl oxidase activities were present on the cloned insert (Chang, H. C., et al., J. Food Sci. 60:551,552 (1995)). In an effort to locate the genes encoding these activities, the transformant was subcloned into 8.2, 3.8 and 0.6 kb HindIII fragments. The transformant EC418 containing the 3.8 kb HindIII insert proved able to grow on limonene, indicating that genes facilitating limonene catabolism in E. coli were retained on this fragment. GC/MS analysis of cell supernatants indicated that perillyl alcohol, α-terpineol, and lesser amounts of carveol were produced, suggesting that both methyl oxidase and hydratase activities were encoded (Table 1).

TABLE 1

Monoterpene Products Produced by Recombinant EC418 During Growth on Limonene

| | Metabolites and concentration (mg/l*) | | |
|---|---|---|---|
| Growth stage | α-terpineol | Carveol | Perillyl alcohol |
| Early log phase (6 h) | 0.7 | 2.6 | 0.7 |
| Late log phase (24 h) | 1.1 | 1.7 | 2.5 |
| Stationary phase (48 h) | 29 | 0.9 | 72 |

The limonene hydratase gene was further subcloned as a 1.7-kb HindIII-BglII fragment as EC419 that expressed hydratase activity, but did not confer growth on limonene nor produce perillyl derivatives. Transformant EC421 carrying the adjacent 2.2-kb BglII-Hind III fragment, demonstrated production of perillyl alcohol and growth on limonene, indicating the presence of the gene(s) encoding limonene methyl oxidation. Surprisingly, limonene hydratase activity was also found with transformant EC423, indicating the presence of two distinct limonene hydratase genes in EC409A.

Preliminary Characterization of the Limonene Hydratase

The limonene hydratase in crude extracts demonstrated broad substrate specificity, in that in addition to hydration of limonene, the nitrile group of cyanopyridine could also be hydrated. Since the latter substrate is more soluble and less volatile than limonene, hydration of cyanopyridine to nicotinamide was utilized for standard assay using a published HPLC procedure (Nagasawa, T., et al., Appl. Environ. Microbiol. 54:1766–1769 (1988)). It was found that the hydratase enzyme expressed from EC419 was thermally unstable, demonstrating no enzymatic activity above 40° C. whereas the hydratase expressed by EC423 exhibited an optimum temperature near 55° C. which is close to the optimum growth temperature of the thermophile parent (data not shown). During preliminary attempts at purification the EC423 enzyme could be pelleted by prolonged ultracentrifugation, suggesting that the enzyme may be membrane bound as previously reported for the limonene hydratase of *Pseudomonas gladioli* (Cadwallader, K. R., et al., in Food Science and Human Nutrition, Charalambous, G., ed., Elsevier, New York 57(1):241–244 & 248 (1992)).

Whole Cell Bioreactor Studies

Figure 3:
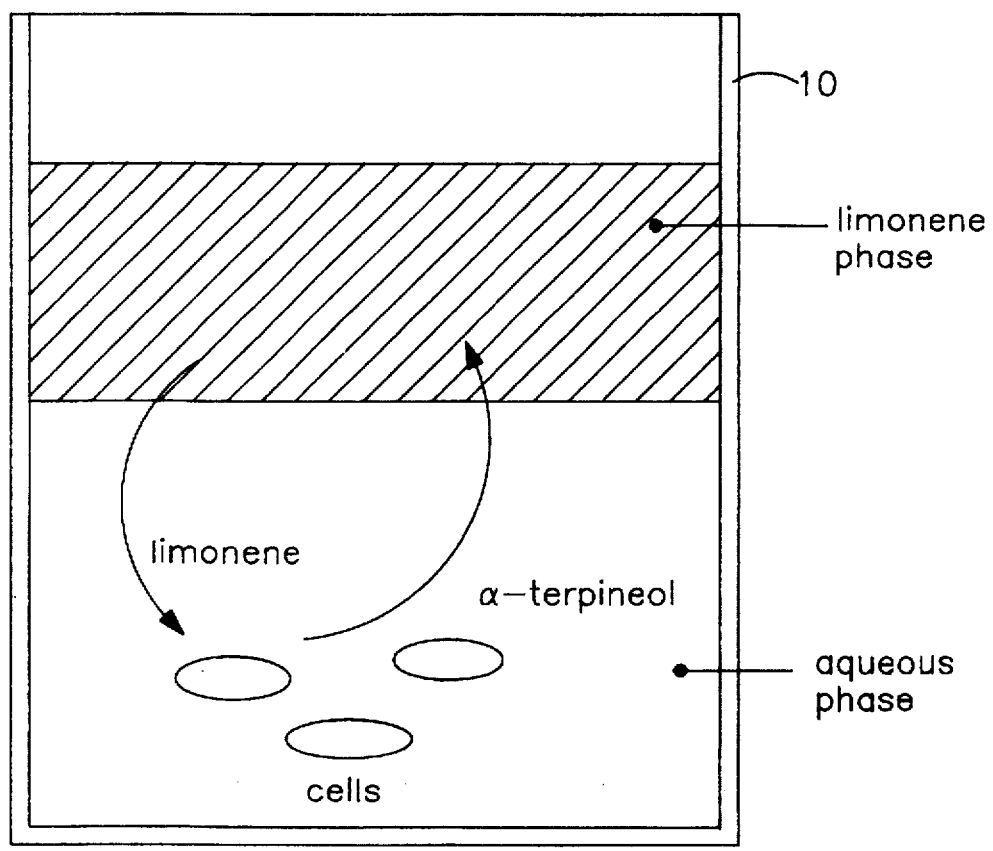
FIG. 3 is a schematic view of a bioreactor for producing monoterpene derivatives from limonene.

An attempt was made to utilize whole cells of *E. coli* EC423 in a two-phase bioreactor at elevated temperature as shown in FIG. 3. Neat limonene was utilized as the organic phase to maintain a saturated level of substrate and to facilitate product removal from the aqueous phase. Both actions serve to prevent dehydration of the α-terpineol product in this reversible reaction. As seen in Table 2, significant accumulation of α-terpineol was achieved with this simple bioreactor system.

TABLE 2

Monoterpene Products Produced by Recombinant
EC423 Utilizing Neat Limonene in a Two-Phase Bioreactor

| Product | Temperature | Concentration (mg/l) Incubation Time (h) | | |
|---|---|---|---|---|
| | | 24 | 48 | 72 |
| α-terpineol | 40° C. | 16 | 117 | 215 |
| | 50° C. | 19 | 168 | 235 |
| | 60° C. | 16 | 201 | 209 |
| Carvine | 40° C. | 3.9 | 20 | 23 |
| | 50° C. | 8 | 21 | 35 |
| | 60° C. | 17 | 19 | 28 |

Concentrations of product determined in the limonene phase are expressed per liter of aqueous cell suspension.

Surprisingly, the monoterpene and carvone were also found in lesser, but significant amounts. Although minor amounts of carveol were produced during limonene utilization by EC418, production of carvone was not observed with either the parental thermophile or the recombinant EC409A containing the same DNA as part of a larger fragment. For both monoterpene products, optimal production occurred at 50° C., with carvone appearing at earlier times.

Discussion

Cloning of the limonene degradative pathway provides an opportunity for separate examination and utilization of the conversion steps for production of valuable monoterpene metabolites. In this report, we have separated the limonene hydration and methyl oxidation steps, and have obtained additional evidence suggesting that the latter step participates in limonene utilization by the recombinant.

Although formation of carvone has been reported previously for other limonene-degrading bacteria (Krasnobajew, V., in Biotechnology, Vol. 6a, Lieslich, K. ed., Verlag Chemie, Weinheim (1984)), formation of this metabolite was not observed during studies of the parental thermophile, and was, therefore, unexpected. From subcloning studies, the gene encoding this ring oxidation activity appears to be distinct separate from that oxidizing the C-1 limonene methyl group. Since carvone is utilized as an important food flavoring (Bauer, K., et al., Common fragrance and flavor materials, VCH, Weinheim (1990)), the enzyme and the encoding gene(s) merit further investigation.

The present invention represents the first attempt to utilize whole cells with thermostable enzymes in a two-phase bioreactor system at elevated temperature. The provision of excess monoterpene substrate and removal of reactive product facilitated by the separate phase provides production of the specialty chemicals α-terpineol and carvone using elevated temperature. The introduction of thermostable enzymes catalyzing biotransformation at elevated temperature into a mesophilic bacterial host also helps to eliminate undesired side reactions catalyzed by host enzymes while retaining advantages of whole cell utilization.

It is intended that the foregoing description be only illustrative of the present invention and that the present invention be limited only by the hereinafter appended claims.

We claim:

1. In a method for microbial or enzymatic degradation of limonene in an aqueous culture medium to produce monoterpene derivatives, the improvement which comprises:

simultaneously with the degradation, extracting the monoterpene derivatives from the aqueous culture medium with a non-water miscible organic solvent for the monoterpene derivatives using a liquid-liquid contact for the extraction.

2. The method of claim 1 wherein the solvent is limonene.

3. The method of claim 1 wherein the microorganism is *Bacillus stearothermophilus*.

4. The method of claim 1 wherein the microorganism is a recombinant *Escherichia coli*.

5. The method of claim 1 wherein the aqueous culture medium is at a temperature of between about 40° and 60° C.

6. The method of claim 3 wherein the *Bacillus stearothermophilus* is deposited as ATCC 55596.

7. The method of claim 1 wherein one of the monoterpene derivatives is carveol.

8. The method of claim 1 wherein one of the monoterpene derivatives is carvone.

9. The method of claim 1 wherein one of the monoterpene derivatives is perillyl alcohol.

10. The method of claim 1 wherein one of the monoterpene derivatives is α-terpineol.

11. The method of claim 4 wherein the *Escherichia coli* is deposited as ATCC 69817.

\* \* \* \* \*